United States Patent [19]

Penco et al.

[11] 4,218,440
[45] Aug. 19, 1980

[54] ANTITUMORDEOXY-ANTHRACYCLINES AND USE THEREOF

[75] Inventors: Sergio Penco, Milan; Giuliano Franchi, Corsico; Federico Arcamone, Nerviano, all of Italy

[73] Assignee: Farmitalia Carlo Erba S.p.A., Milan, Italy

[21] Appl. No.: 941,920

[22] Filed: Sep. 13, 1978

[30] Foreign Application Priority Data

Sep. 5, 1978 [IT] Italy .............................. 23152 A/78

[51] Int. Cl.$^2$ ...................... A61K 31/71; C07H 15/24
[52] U.S. Cl. .................................. 424/180; 536/17 A
[58] Field of Search ............... 424/180; 536/17 A, 17, 536/9, 8

[56] References Cited

U.S. PATENT DOCUMENTS

| | | | |
|---|---|---|---|
| 3,087,821 | 4/1963 | Horowitz et al. ...................... 536/8 |
| 4,020,270 | 4/1977 | Arcamone et al. ................. 536/17 A |
| 4,035,566 | 7/1977 | Israel et al. .......................... 536/17 A |

*Primary Examiner*—Johnnie R. Brown

*Attorney, Agent, or Firm*—Hubbell, Cohen, Stiefel & Gross

[57] ABSTRACT

Compounds having the formula:

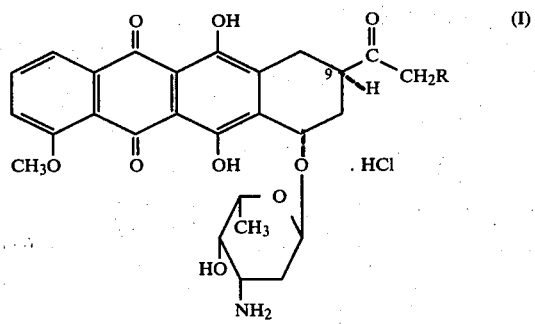

wherein R is H or OH, and which are useful in treating certain mammalian tumors, are prepared from 9,10-anhydro-N-trifluoroacetyldaunorubicin, a known compound.

2 Claims, No Drawings

ANTITUMORDEOXY-ANTHRACYCLINES AND USE THEREOF

The invention described herein was made in the course of work under a grant from the U.S. Department of Health, Education and Welfare.

BACKGROUND OF THE INVENTION

1. Field of the Invention

The present invention relates to new antitumor glycosides of the anthracycline series, processes for their preparation and the use thereof.

2. The Prior Art

Daunorubicin (also known as daunomycin) and doxorubicin (also known as adriamycin), of which the present compounds are derivatives, are known and are known to be useful in treating certain mammalian tumors.

The compound 9,10-anhydro-N-trifluoroacetyldaunorubicin (II), which is the starting material for the compounds of the present invention is a known compound which is described in British Patent Specification No. 53456/76, owned by the unrecorded assignee hereof.

SUMMARY OF THE INVENTION

The present invention provides, in one aspect thereof, a new class of compounds having the formula:

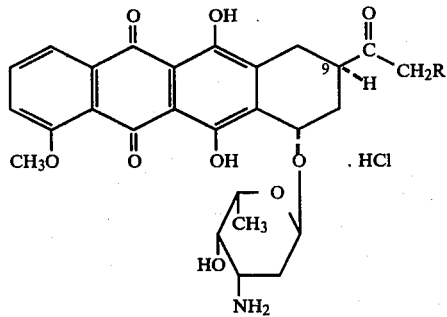

wherein R is H or OH.

In another aspect, the invention provides a novel method of making these compounds starting from 9,10-anhydro-N-trifluoroacetyldaunorubicin (II):

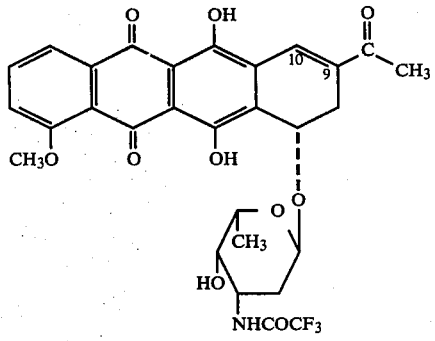

According to this method, first the C-9,10 double bond in compound (II) is stereospecifically reduced. The reduction is effected by dissolving (II) in a suitable aprotic solvent such as dioxane, tetrahydrofuran, chloroform, acetonitrile or dimethylformamide and hydrogenating same with a reducing agent such as lithium aluminum hydride or hydrogen in the presence of a metallic catalyst. Preferably, (II) is dissolved in dioxane and hydrogenated in the presence of 5% palladium on barium sulphate. A subsequent mild alkaline treatment, in order to hydrolyze the N-protecting group, followed by chromatographic purification, affords 9-deoxydaunorubicin (I; R=H), which is isolated as the hydrochloride, in 20% over-all yield. 9-Deoxydoxorubicin (I; R=OH) is prepared from 9-deoxydaunorubicin via its 14-bromoderivative, according to the procedure described in U.S. Pat. No. 3,803,124. The new compounds of formula (I) display antimitotic activity and are useful therapeutic agents for the treatment of tumor diseases in mammals.

Thus, in yet another aspect, the invention provides a method of treating certain mammalian tumors by administering to a host afflicted therewith, a therapeutically effective amount of a compound of formula (I).

DESCRIPTION OF THE PREFERRED EMBODIMENTS

The following examples are given to better illustrate the invention without, however, limiting same.

EXAMPLE 1

9-Deoxy-daunorubicin (I; R=H)

2.0 Grams of 9,10-anhydro-N-trifluoroacetyldaunorubicin (II), dissolved in 150 ml. of dioxane were hydrogenated at room temperature and pressure in the presence of 4.0 g. of 5% Pd on BaSO$_4$. The reduction was carefully monitored on thin layer chromatography (TLC) using Kieselgel Merck plates F$_{254}$ and, as a solvent system: CHCl$_3$:(CH$_3$)$_2$CO (4:1 v/v). Such monitoring of the course of the reduction is necessary in order to avoid hydrogenolysis of the glycosidic linkage. Thus, the reduction was interrupted when the amount of the residual starting material was about 20%. The crude product, obtained after filtration and evaporation of the solvent, was dissolved in 30 ml. of acetone and treated at 0° C. with 300 ml. of 0.1 N aqueous NaOH. Then the pH of the solution was adjusted to 8.3 and the solution was extracted repeatedly with chloroform. The combined organic (chloroform) extracts were dried over anhydrous Na$_2$SO$_4$, evaporated to a residue under vacuum and the residue was purified by chromatography on a column of silicic acid using the solvent system: CHCl$_3$:CH$_3$OH:H$_2$O (10:2:0.2 v/v) as the eluting agent.

The fractions containing 9-deoxydaunorubicin, in the form of the free base were combined and extracted with 0.1 N aqueous HCl. The acidic, aqueous red solution was separated, adjusted to pH 8.3 with aqueous 0.5 N NaOH and extracted with chloroform until the red product was completely transferred to the organic phase. Finally, the combined chloroform extracts were dried over anhydrous Na$_2$SO$_4$, evaporated under vacuum to a small volume (about 20 ml.) and acidified to pH 3.5 with anhydrous hydrogen chloride. Addition of excess diethyl ether precipitated 0.4 g. of 9-deoxydaunorubicin hydrochloride, m.p. 162° (dec.); TLC on Kieselgel Merck F$_{254}$ plates; solvent system: CHCl$_3$:CH$_3$OH:H$_2$O (10:2:0.2 v/v): Rf 0.25.

Elemental Analysis: for C$_{27}$H$_{30}$ClNO$_9$: Calculated: H 5.53; C 59.17; N 2.56; Cl 6.47; Found: H 5.64; C 58.60; N 2.48; Cl 6.47.

EXAMPLE 2

9-Deoxydoxorubicin (I; R=OH)

By treating 0.7 g. of 9-deoxydaunorubicin in accordance with the method described in U.S. Pat. No. 3,803,124, there was obtained 0.37 g. of 9-deoxydoxorubicin hydrochloride (II; R=OH); m.p. 170° C. (dec.). TLC on Kieselgel Merck $F_{254}$ plates; solvent system: $CHCl_3:CH_3OH:H_2O$ (13:6:1 v/v): Rf 0.26.

Elemental Analysis for $C_{27}H_{30}ClNO_{10}$:
Calculated: H 5.37; C 57.49; Cl 6.29;
Found: H 5.17; C 57.57; Cl 6.21.

BIOLOGICAL ACTIVITY

The compounds according to the invention were tested under the auspices of NCI-National Institute of Health, Bethesda, Maryland against lymphocytic leukemia $P_{388}$ according to the procedure described in Cancer Chemotherapy Reports, Part 3, vol. 3, page 9 (1972). The data reported in the following table, show the antitumor activity of the compounds of the invention.

TABLE

Antitumor activity of deoxydaunorubicin and 9-deoxydoxorubicin compared with daunorubicin and doxorubicin

| Compound | Dose (mg./kg.) | T/C % |
| --- | --- | --- |
| Daunorubicin | 16 | 107 |
| | 8 | 131 |
| | 4 | 121 |
| | 2 | 118 |
| 9-Deoxydaunorubicin | 50 | 128 |
| | 25 | 136 |
| | 12.5 | 115 |
| | 6.25 | 102 |
| Doxorubicin | 16 | 108 |
| | 8 | 171 |
| | 4 | 133 |
| | 2 | 129 |
| | 1 | 119 |
| 9-Deoxydoxorubicin | 50 | 108 |
| | 25 | 106 |
| | 12.5 | 117 |
| | 6.25 | 101 |
| | 3.13 | 106 |

The compounds were tested in vivo on CDF mice infected with tumor cells. The i.p. injections were made on days 5, 9 and 13 (4 days interval between each injection) starting from the fifth day after tumor transplantation in the mice. The median survival time expressed as percent of controls (T/C %) are reported.

Variations and modifications can, of course, be made without departing from the spirit and scope of the invention.

Having thus described our invention, what we desire to secure by Letters Patent and hereby claim is:

1. A method of treating a host afflicted with transplanted lymphocytic leukemia $P_{388}$ comprising administering to a host afflicted therewith, a therapeutically effective amount of a compound of the formula:

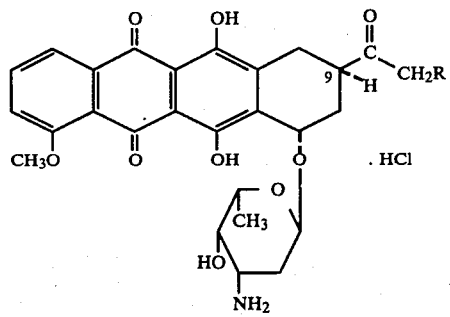

wherein R is H or OH.

2. A method according to claim 1, wherein said compound is administered intraperitoneally.

UNITED STATES PATENT OFFICE
CERTIFICATE OF CORRECTION

Patent No. 4,218,440   Dated August 19, 1980

Inventor(s) Penco et al.

It is certified that error appears in the above-identified patent and that said Letters Patent are hereby corrected as shown below:

Column 3, line 29: "deoxydaunorubicin" should read -- 9-deoxydaunorubicin --.

Signed and Sealed this

Third Day of March 1981

[SEAL]

Attest:

RENE D. TEGTMEYER

Attesting Officer    Acting Commissioner of Patents and Trademarks